(12) United States Patent
Ripplinger

(10) Patent No.: US 11,744,632 B2
(45) Date of Patent: Sep. 5, 2023

(54) GENERATOR WITH REGENERATION DEVICE

(71) Applicant: Erbe Elektromedizin GmbH, Tuebingen (DE)

(72) Inventor: Thomas Ripplinger, Tuebingen (DE)

(73) Assignee: ERBE Elektromedizin GMBH, Tuebingen (DE)

( * ) Notice: Subject to any disclaimer, the term of this patent is extended or adjusted under 35 U.S.C. 154(b) by 0 days.

(21) Appl. No.: 17/870,453

(22) Filed: Jul. 21, 2022

(65) Prior Publication Data

US 2023/0024523 A1    Jan. 26, 2023

(30) Foreign Application Priority Data

Jul. 26, 2021   (EP) ..................... 21187788

(51) Int. Cl.
  *A61B 18/12*   (2006.01)
  *A61B 18/00*   (2006.01)

(52) U.S. Cl.
  CPC ..... *A61B 18/1206* (2013.01); *A61B 2018/00702* (2013.01); *A61B 2018/128* (2013.01); *A61B 2560/0209* (2013.01)

(58) Field of Classification Search
  CPC ......... H03B 2202/07; H03B 2202/073; H03B 2202/076; H03B 5/124; A61B 18/1206; A61B 2018/00702; A61B 2018/128; A61B 2560/0209
  See application file for complete search history.

(56) References Cited

U.S. PATENT DOCUMENTS

| | | | |
|---|---|---|---|
| 4,281,373 A | 7/1981 | Mabllle | |
| 4,429,694 A | 2/1984 | McGreevy | |
| 5,167,600 A | 12/1992 | Altendorf | |
| 6,238,387 B1 * | 5/2001 | Miller, III | A61B 18/1206 606/42 |
| 6,261,286 B1 | 7/2001 | Goble et al. | |
| 2005/0143725 A1 | 6/2005 | Daners et al. | |
| 2012/0053578 A1 * | 3/2012 | Schall | A61B 18/1206 606/33 |
| 2014/0018795 A1 | 1/2014 | Shilev et al. | |
| 2018/0042660 A1 | 2/2018 | Assmus et al. | |

FOREIGN PATENT DOCUMENTS

| | | |
|---|---|---|
| DE | 40 09 819 A1 | 10/1991 |
| DE | 100 46 592 A1 | 4/2002 |
| DE | 100 46 592 C2 | 12/2002 |
| EP | 1 499 254 B1 | 6/2008 |
| EP | 2 424 458 B1 | 6/2019 |
| JP | H08299356 A | 11/1996 |
| WO | WO 98/07378 A1 | 2/1998 |
| WO | WO 98/27880 A1 | 7/1998 |
| WO | WO 03/090635 A1 | 11/2003 |

\* cited by examiner

*Primary Examiner* — Joanne M Rodden
*Assistant Examiner* — Sean W Collins
(74) *Attorney, Agent, or Firm* — Blank Rome LLP

(57) ABSTRACT

An electrosurgical generator having an oscillating circuit that is excited by an excitation circuit with a frequency preferably close to the resonance frequency of the oscillating circuit. A regeneration circuit, which may be a voltage multiplier circuit, is used to stop the oscillation as suddenly as possible without losing the energy stored in the oscillating circuit.

15 Claims, 2 Drawing Sheets

GENERATOR WITH REGENERATION DEVICE

CROSS-REFERENCE TO RELATED APPLICATION

This application claims priority to European Application No. 21187788.1, filed Jul. 26, 2021, the entirety of which is incorporated by reference herein.

TECHNICAL FIELD

Embodiments of the invention described herein are directed to an electrosurgical generator having a regeneration device.

BACKGROUND

Electrosurgical generators provide typically a radiofrequency electrical voltage for operation of an electrical instrument. Such generators often comprise an oscillating circuit that provides the radiofrequency electrical voltage and the radiofrequency electrical current for supply of the electrosurgical instrument. In many cases the radiofrequency voltage has to be modulated in order to achieve specific surgical purposes.

Such a generator is known from DE 100 46 592 A1 in which a radiofrequency electrical voltage is amplitude modulated by means of a square wave. At the end of an oscillating cycle of the oscillating circuit the oscillation has to be stopped as fast as possible. DE 100 46 592 A1 proposes a damping circuit for this purpose. It comprises an inductor that is in transformer-type coupling with the oscillating circuit inductor of the generator and that provides energy removed from the oscillating circuit to a damping resistor that transfers the energy into heat. In doing so, the attenuation of the oscillation of the generator oscillating circuit is accelerated and the oscillation is stopped quickly.

By means of this method good modulation of a surgical voltage can be achieved indeed, but a high energy consumption is correlated therewith.

As remedy EP 2 424 458 B1 proposes to provide, instead of a resistor, a regeneration circuit for elimination of the energy contained in the oscillating circuit that feeds the energy back to a storage capacitor at the end of an RF impulse and transforms only a rest of energy into heat in an ohmic resistor that cannot be fed back onto the storage capacitor anymore. In doing so, the process of stopping the oscillation of the oscillating circuit is carried out in two phases. In a first phase energy of an oscillating circuit is regenerated on a storage capacitor and in a second phase a rest of energy still contained in the oscillating circuit is transformed into heat. With this concept a higher energy efficiency can be achieved. However, still energy portions have to be eliminated. In addition, the desire exists for a more efficient and faster damping of the oscillating circuit.

Further prior art is DE 40 09 819 A1, U.S. Pat. No. 4,429,694, JP H 08-2 99 356, WO 98/07378 A1, WO 03/090635, U.S. Pat. No. 4,281,373 A, WO 98/27880, DE 10 046 592 A1 and U.S. Pat. No. 6,261,286 B1.

SUMMARY

Starting therefrom it is an object of embodiments of the invention to provide a generator with improved regeneration circuit.

This object may be solved by means of a generator according to, for example, claim 1.

The generator according to embodiments of the invention comprises a regeneration circuit that can be activated and deactivated in a controlled manner. For example, a respective switching element serves for controlled activation and deactivation. If activated, the regeneration circuit connects the oscillating circuit of the electrosurgical generator with a buffer capacitor in order to feed back energy from the oscillating circuit into the supply circuit and particularly onto the buffer capacitor that is provided there. According to embodiments of the invention, the regeneration circuit comprises a voltage multiplier circuit, particularly a voltage multiplier circuit that is realized by a capacitor-diode-combination. When it is activated, the voltage multiplier circuit removes electrical energy from the oscillating circuit and thereby builds up a voltage increasing with each oscillation that is a multiple of the voltage removed from the oscillating circuit. The amount of the voltage multiplication is obtained from the number of stages of the voltage multiplier circuit. By means of the voltage multiplication, the energy present in the oscillating circuit is very quickly and efficiently regenerated onto the buffer capacitor, whereby the damping of the oscillating circuit is still maintained, if the voltage in the oscillating circuit is less than the supply voltage. In addition, the voltage of the buffer capacitor can increase during regeneration without impeding the regeneration process.

The concept according to embodiments of the invention particularly eliminates the need of a damping resistor for damping of voltage residuals in the oscillating circuit. In doing so, the generator according to embodiments of the invention allows an operation in which the radiofrequency voltage of the oscillating circuit can be in the range of 100 kHz up to multiple MHz with high modulation frequencies in the range of some 10 kHz, e.g. 20 kHz, 40 kHz, 60 kHz, 80 kHz or also above. In addition, particularly the energy efficiency of modes is improved in which the switch-on duration of the RF impulse is respectively very short, as for example in cutting modes, in which the pulse-pause-ratio of the modulated RF voltage is particularly low.

Typically the oscillating circuit is a parallel oscillating circuit that consists of at least one oscillating circuit inductor and at least one oscillating circuit capacitor. Assigned to the oscillating circuit is an excitation circuit that is configured to excite the oscillating circuit at its resonance frequency. In the simplest case the excitation circuit comprises one controlled switch that supplies energy to the parallel oscillating circuit in impulses. However, the excitation circuit can also comprise multiple controlled switches, e.g. in a half-bridge circuit or in a bridge circuit.

The supply circuit is preferably a direct voltage source that comprises a storage capacitor arranged at its output. The direct voltage source can be a voltage converter circuit, such as a PFC circuit (Power Factor Correction circuit). A flyback converter can serve for this purpose. The PFC circuit supplies substantially constant direct voltage from a pulsating rectified grid alternating voltage. Other converter circuits can also be used.

The storage capacitor arranged at the output of the supply circuit forms a buffer that absorbs the energy supplied by the regeneration circuit. It is then again available for supply of the oscillating circuit.

The regeneration circuit can be directly connected with the oscillating circuit inductor. Alternatively, the regeneration circuit can be connected with a regeneration inductor that is in transformer-type coupling with the oscillating circuit inductor. In both cases the voltage multiplier circuit effects an increase of the voltage derived from the oscillating circuit and thus an efficient energy regeneration.

Preferably the voltage multiplier circuit is a so-called capacitor cascade, particularly a multiple stage cascade. Such a circuit comprises two series circuits of multiple capacitors respectively, whereby the connection points of the capacitors of each series circuit are connected with the connection points of the respective other series circuit of capacitors via a diode chain arranged in a zigzag. For activating or deactivating of the voltage multiplier circuit a switch is preferably provided. It is preferably arranged between the regeneration inductor or the oscillating circuit capacitor and the voltage multiplier circuit. This concept minimizes the capacitive coupling between the regeneration circuit and the oscillating circuit in case of inactive regeneration circuit and thus allows an undisturbed operation of the generator outside regeneration phases. The switch is preferably configured and controlled such that the regeneration circuit is only connected with the oscillating circuit during the regeneration phases.

The generator according to embodiments of the invention preferably comprises a control circuit that is configured to alternatingly activate the excitation circuit on one hand and the regeneration circuit on the other hand. Thereby the oscillation of the oscillating circuit can be switched on and off such that a nearly perfect square wave modulation of the RF output voltage of the generator becomes possible. Other types of modulation, e.g. saw tooth modulation, are possible. Embodiments of the invention provides advantages, if the desired modulation requires steep back flanks, i.e. a quick stop of the RF oscillation.

BRIEF DESCRIPTION OF THE DRAWINGS

Further details of advantageous embodiments are subject to dependent claims as well as the description and the associated drawing. The drawing shows:

DETAILED DESCRIPTION

Figure 1:
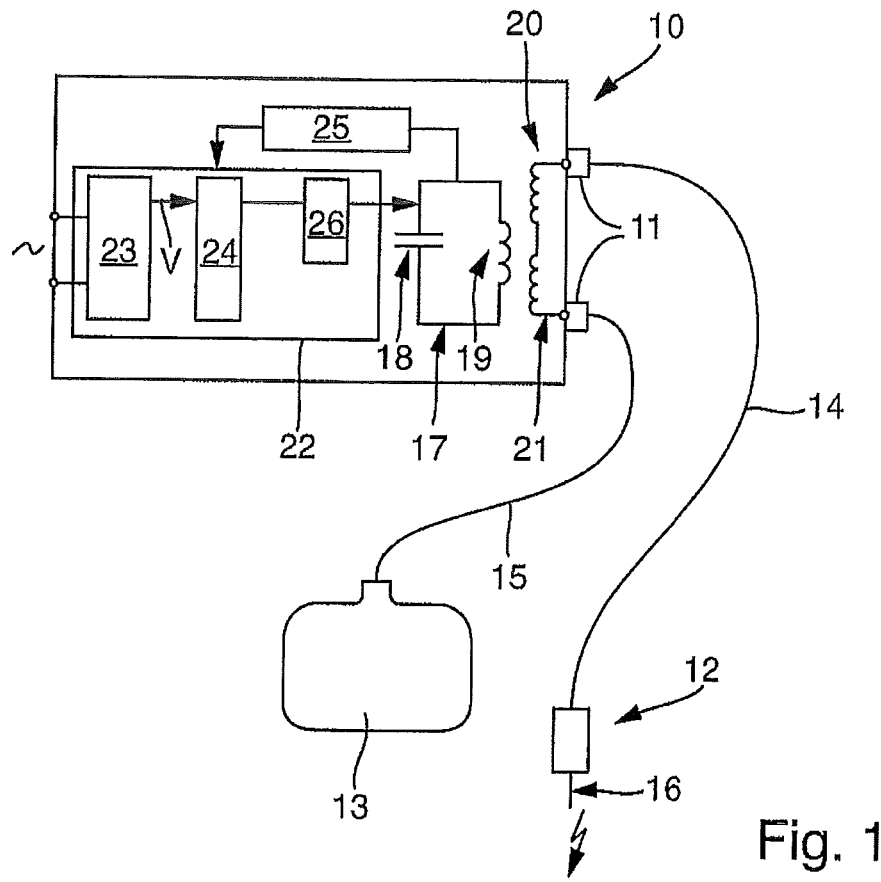
FIG. 1 the generator according to an embodiment of the invention with a connected instrument in a schematic overview illustration, FIG. 2 a simplified circuit diagram of the generator according to FIG. 1, FIG. 3 a circuit diagram of a modified generator according to FIG. 1, FIG. 4 another partly schematic circuit diagram of a generator according to FIG. 1, and FIG. 5 a diagram for illustrating the oscillating behavior of the generator according to FIGS. 1-4.

FIG. 1 illustrates a generator 10 for providing a surgical voltage at an output 11. A bipolar surgical instrument or, as illustrated in FIG. 1, a monopolar surgical instrument as well as a neutral electrode 13 can be connected thereto. The instrument 12 as well as the neutral electrode 13 can be connected with the output 11 via respective lines 14, 15.

The instrument 12 comprises at least one electrode 16 with which biological tissue of the patient is to be influenced. On the contrary, the neutral electrode 13 is configured extensively in order to allow a current flow between the patient and the neutral electrode 13 without physiological effect.

In FIG. 1 the instrument 12 is schematically illustrated. It can be a cutting instrument, a coagulation instrument as well as any other monopolar or bipolar electro-surgical instrument. In case of a bipolar instrument it comprises two electrodes that are both connected via respective lines or a cable with the output 11.

The generator 10 is particularly suitable for supply of instruments that have to be supplied with a pulsed electrical radiofrequency voltage. A pulsed electrical radiofrequency voltage (RF voltage) means particularly voltages that have a basic frequency between 100 kHz and 5 MHz, preferably 300 kHz to 500 kHz, and that are amplitude modulated by means of a square wave impulse sequence. This means that the amplitude of the RF voltage generated by generator 10 alternates with a frequency of the square wave pulse sequence in its value between a first value and a second value, e.g. between multiple 100 Volts and 0 Volts or between multiple 100 Volts and only multiple 10 Volts. The RF voltage is thus, for example, an "on/off-switched" voltage. However, embodiments of the invention are also suitable for the creation of an RF voltage with other modulation shapes, e.g. RF voltage with saw tooth modulation and all other modulation shapes, particularly those in which it is of importance that the RF oscillation at the end of an RF voltage impulse stops quickly.

The structure of generator 10 is illustrated in a kind of overview in FIG. 1. For creation of the desired radiofrequency alternating voltage serves an oscillating circuit 17 that comprises at least one oscillating circuit capacitor 18 and at least one oscillating circuit inductor 19 that are connected parallel to one another.

In order to supply electrical radiofrequency energy to the instrument 12, the oscillating circuit 17 is connected with a decoupling circuit 20 that is realized in the present embodiment by means of at least one decoupling inductor 21 that is magnetically (transformatorically) coupled with the oscillating circuit inductor 19. Other decoupling circuits are possible. The decoupling inductor 21 can consist of multiple sub-inductors that are connected with each other in series. Preferably the oscillating circuit inductor 19 and the decoupling inductor 21 thus form a transformer having a transfer factor larger than 1. The transfer factor is the ratio of the number of windings of the decoupling inductor 21 relative to the number of windings of the oscillating circuit inductor 19.

For excitation and for sustain of an oscillation in the oscillating circuit 17, an excitation circuit 22 is provided that supplies excitation energy to the oscillating circuit 17. The excitation circuit 22 comprises a direct voltage source 23 for providing of direct voltage power. A line supplying a respective direct voltage V is connected to a buffer capacitor 24. The latter serves for storage of energy and also for absorption of energy that is regenerated from the oscillating circuit 17 in case of stopping the RF oscillation of the oscillating circuit 17.

A regeneration circuit 25 is provided for regeneration of energy from the oscillating circuit 17 when stopping the RF oscillation. It connects the oscillating circuit 17 with the buffer capacitor 24 in order to regenerate energy onto the buffer capacitor 24 whenever the oscillation of the oscillating circuit 17 shall be stopped as quickly as possible.

Figure 2:
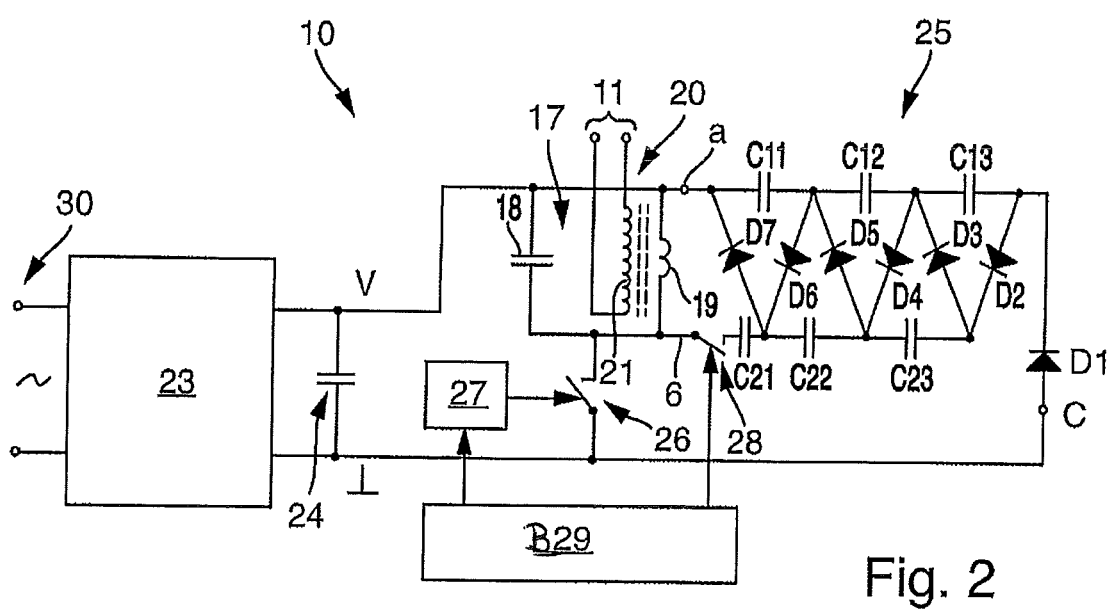

FIG. 2 illustrates the circuit diagram of generator 10, particularly also of regeneration circuit 25 in more detail. As apparent, the excitation circuit 22 can be realized in the simplest case by an electronically controlled switch 26 and a control circuit 27 associated thereto. The switch 26 is arranged between the oscillating circuit 17 or a regeneration inductor 29 (FIG. 3) and an input of the re-generation circuit 25. If it is conducting, the regeneration circuit 25 is active and supplies energy from the oscillating circuit 17 under damping thereof back onto the buffer capacitor 24. If it blocks, the regeneration circuit is inactive and does not damp the oscillating circuit 17.

The regeneration circuit 25 can be directly connected to the oscillating circuit 17. Thereby its two input lines a, b can be directly connected with the input of the regeneration circuit. Lines a and c thereby form the output of the regeneration circuit 25.

The regeneration circuit 25 is preferably a voltage multiplier circuit. It comprises two branches with series connections of multiple capacitors respectively, e.g. 2, 3 or 4 or more capacitors. In one branch capacitors C11, C12, C13 are connected with each other in series. In the other branch extending parallel thereto capacitors C21, C22, C23 provided in equal number are connected with one another in series. The connection points between the respective capacitors of the two branches are connected to each other by means of diodes, such that a common voltage multiplier circuit is created. The diodes D1 to D7 are arranged in a zigzag between the branches formed by capacitors C11 to C13 and C21 to C23. The diodes D1 to D7 are connected in series with identical polarity, i.e. at each connection point the anode of one diode and the cathode of the other diode are connected to each other.

An activation switch 28 arranged in line b is part of the regeneration circuit 25. Line b forms a connection between the oscillating circuit 17 and the regeneration circuit 25. The activation switch is configured to open and close a current path in line b.

Activation switch 28 and the electronic switch 26 are controlled in coordinated manner. For the control a control device B29 can be provided that controls switches 26, 28 directly or also via interposition of control circuits, such as the control circuit 27. The control circuit opens and closes the switch 26 in sync with the oscillation of the oscillating circuit 17 as long as it shall be excited. If the oscillation shall be stopped, the switch 26 remains in non-conductive condition and the switch 28 is transferred into the conductive condition. If the oscillating circuit shall restart to oscillate, the switch 28 is transferred into the non-conductive condition and the switch 26 is again switched on and off with a switching frequency according to the resonance frequency of the oscillating circuit 17.

Figure 3:
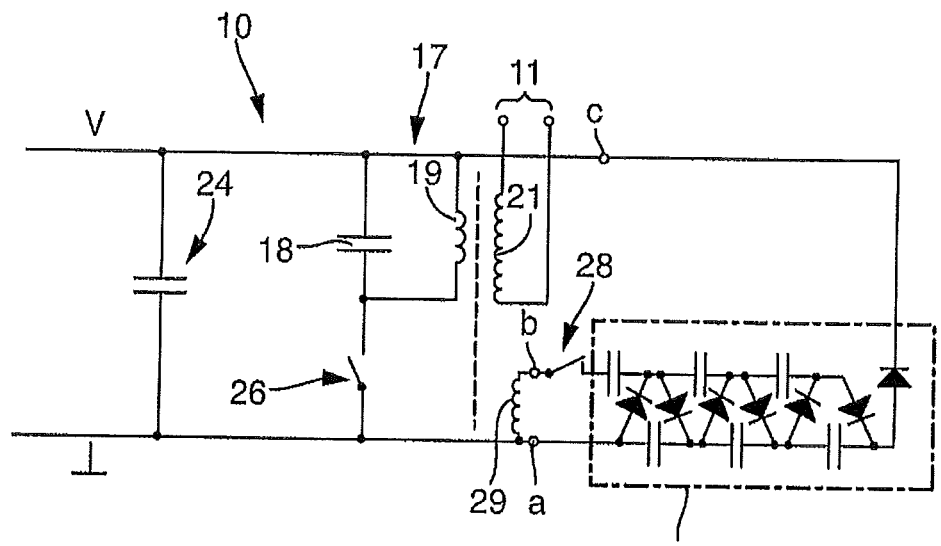

A modified embodiment of generator 10 is illustrated in FIG. 3. With regard to the basic description, the explanations above apply accordingly on the basis of the already introduced reference signs:

While the lines a and b of the regeneration circuit 25 are directly connected with the oscillating circuit in the embodiment according to FIG. 2, the lines a and b are connected with a regeneration inductor 29 in the embodiment according to FIG. 3 that is coupled with the oscillating circuit inductor 19 in transformer-type manner. The regeneration inductor 29 and the oscillating circuit inductor 19 thus form a transformer having a transfer factor preferably between 1 and 2. Other transfer factors are possible. The transfer factor is defined as ratio between the number of windings of the regeneration inductor 29 and the number of windings of the oscillating circuit inductor 19.

Figure 4:
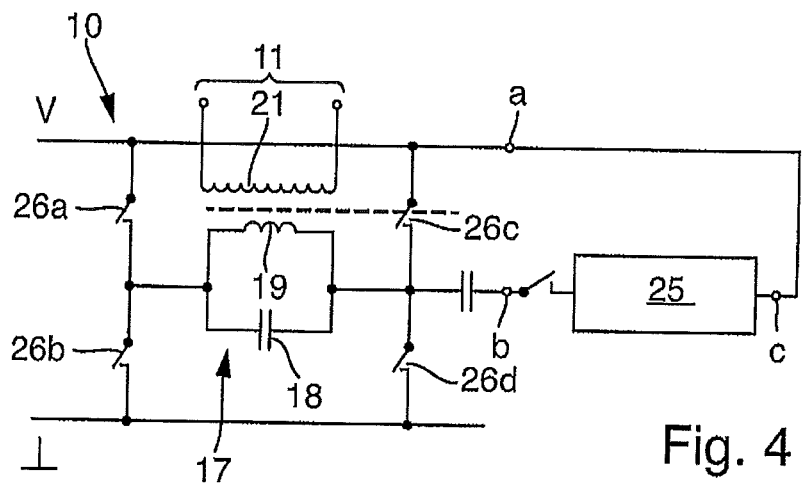

FIG. 4 illustrates a further modification of generator 10. There the excitation circuit comprises multiple switches 26a, 26b, 26c, 26d forming a bridge circuit in order to excite the oscillating circuit 17. FIG. 4 illustrates a full-bridge circuit having four switches 26a-26d. However, also a half-bridge circuit can be used for excitation of the oscillating circuit 17 in which two switches, e.g. the switches 26a, 26b are replaced by capacitors.

The generator 10 according to FIG. 2 described so far operates as follows:

For description of the function it is assumed by way of example only that the oscillating circuit 17 comprises a resonance frequency between 200 kHz and 1 MHz, e.g. 350 kHz, 500 kHz or the like. Accordingly, the control device B29 is provided to open and close the switch 26 with this frequency in order to excite the oscillating circuit 17 with its resonance frequency. The direct voltage source 23 that is, for example, supplied from general power grid 30, provides a direct voltage of, for example, multiple 100 Volts, e.g. 300 V, between ground and the operating voltage line V, such that the buffer capacitor 24 is loaded with operating voltage (e.g. 300 V).

Figure 5:
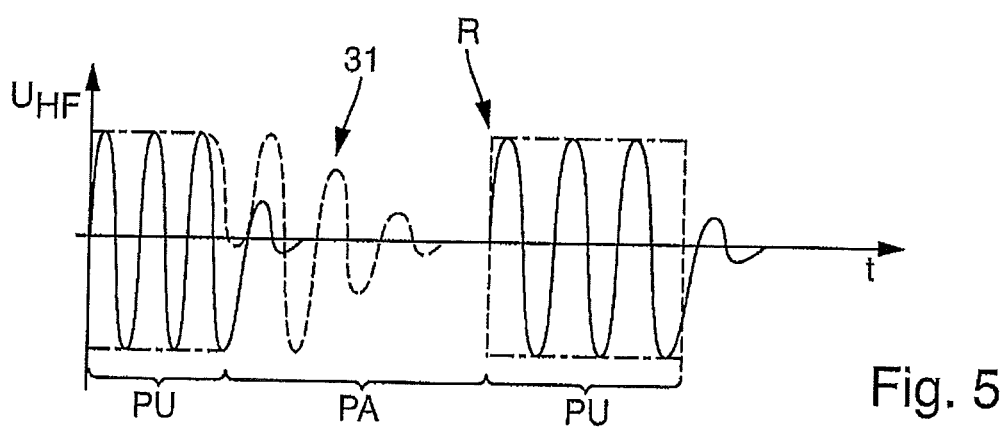

If it is now assumed that the oscillation that is present in the oscillating circuit 17 shall be pulsed with a square wave function R, as illustrated in FIG. 5, oscillating pauses PA have to be created between individual pulses PU. The pulses PU of the RF voltage $U_{HF}$ can have a length of, for example, some microseconds, e.g. 5 µs. The duration of the pauses PA between the individual impulses PU of the RF voltage depends on the modulation frequency and the so-called duty cycle. Particularly in cutting modes, in which the RF can be very high (some 1000 V), while the impulses PU of the RF voltage are very short (one to a few RF oscillations per impulse PU of the RF voltage) the pulse-pause-ratios can be small and thus the duration of the RF-pause PA comparably long (e.g. 100 µs).

In the generator 10 it is important that the RF oscillation at the end of each RF voltage impulse PU is stopped quickly and efficiently so that no or only a few post-pulse oscillation of the oscillating circuit 17 occurs. FIG. 5 illustrates an attenuation curve 31 in dashed lines, as it can occur in a generator without damping by means of the regeneration circuit 25. However, because the control device B29 at the end of an impulse PU of the RF voltage closes the switch 28 and thus activates the regeneration circuit 25, the attenuation process illustrated in solid lines in FIG. 5 is drastically shortened. Thereby it is assumed that the regeneration circuit 25 comprises capacitors C11 to C23 that are loaded due to former regeneration actions. The energy contained in the oscillating circuit 17 is thus transferred on the buffer capacitor 24 with a few oscillations of the oscillating circuit 17. Also with attenuated oscillation amplitude of the oscillating circuit 17 the regeneration process is continued, because the regeneration circuit 25 operates as voltage multiplier circuit and thus increases the voltage decreasing during attenuation of the RF oscillation due to multiplication again up to a value that is sufficient for supply of buffer capacitor 24.

The electrosurgical generator 10 according to an embodiment of the invention comprises an oscillating circuit that is excited by means of an excitation circuit with a frequency that is preferably in the proximity of its resonance frequency, wherein this oscillation shall be interrupted periodically. This can be done, for example, in the context of a pulse-pause-modulation of the radiofrequency voltage UHF that has to be created, the basic frequency of which, e.g. 350 kHz or 500 kHz, can be modulated with a modulation frequency of, for example, 50 kHz. Other modulation frequencies are possible. Typically they are below 100 kHz. In order to stop the oscillation in the oscillating circuit of the generator as suddenly as possible without losing the energy stored in the oscillating circuit 17, a regeneration circuit 25 is provided that is realized by means of a voltage multiplier circuit. Compared with a step-up transforming coupling inductor it has the advantage of a low capacitive load provided to the oscillating circuit 17, particularly because it is connected via switch 28 electrically effectively with the oscillating circuit 17 only in the regeneration phase. This concept allows efficient energy regeneration and thus allows a precise amplitude modulation, particularly square wave modulation (on-off-switching), of the radiofrequency voltage $U_{HF}$.

The invention claimed is:

1. An electrosurgical generator comprising:
   an oscillating circuit connected to an excitation circuit configured to create an electrical oscillation in the oscillating circuit, the oscillating circuit comprising:
   at least one oscillating circuit inductor; and
   at least one oscillating circuit capacitor;
   a direct voltage source connected to a buffer capacitor and configured to provide a supply voltage to the oscillating circuit;
   a decoupling circuit connected to the oscillating circuit and to a connection device for a surgical instrument; and
   a regeneration circuit for transferring energy stored in the oscillating circuit to the buffer capacitor, the regeneration circuit comprising a voltage multiplier circuit.

2. The electrosurgical generator according to claim 1, wherein the oscillating circuit is a parallel oscillating circuit.

3. The electrosurgical generator according to claim 1, further comprising a supply circuit including the direct voltage source, wherein the supply circuit comprises at least one controlled switch.

4. The electrosurgical generator according to claim 1, further comprising a supply circuit including the direct voltage source having the buffer capacitor arranged at its output.

5. The electrosurgical generator according to claim 1, wherein the decoupling circuit comprises a decoupling inductor coupled to the at least one oscillating circuit inductor in a transformer-type manner.

6. The electrosurgical generator according to claim 1, wherein the regeneration circuit comprises a regeneration inductor that is coupled to the at least one oscillating circuit inductor in a transformer-type manner.

7. The electrosurgical generator according to claim 1, wherein the regeneration circuit is connected to the at least one oscillating circuit inductor.

8. The electrosurgical generator according to claim 1, wherein the voltage multiplier circuit is a capacitor cascade.

9. The electrosurgical generator according to claim 8, wherein the capacitor cascade is a multiple stage cascade.

10. The electrosurgical generator according to claim 8, wherein the capacitor cascade comprises two series connections of multiple capacitors respectively, wherein each connection point that is present between two capacitors of one series connection is connected with two diodes arranged anti-parallel that are connected with different connection points of the respective other series connections.

11. The electrosurgical generator according to claim 6, wherein a switch is arranged between the regeneration inductor and the voltage multiplier circuit.

12. The electrosurgical generator according to claim 6, wherein the ratio of the number of windings of the regeneration inductor to the number of windings of the at least one oscillating circuit inductor is between 1 and 2.

13. The electrosurgical generator according to claim 1, further comprising:
    a control device configured to alternatingly activate the excitation circuit and the regeneration circuit.

14. The electrosurgical generator according to claim 11, wherein the switch comprises a semi-conductor switch.

15. The electrosurgical generator according to claim 14, wherein a first end of the regeneration inductor is connected to ground and a second end of the regeneration inductor is connected to the switch.

* * * * *